United States Patent [19]

Quentin et al.

[11] Patent Number: 5,225,532
[45] Date of Patent: Jul. 6, 1993

[54] SYMMETRICAL BIPEPTIDES CONTAINING A POLYALKYLENE GLYCOL RESIDUE, METHOD OF PREPARATION AND USE IN THE ASSAY OF PROTEASES

[75] Inventors: Gérard Quentin, Colombes; Jean-Luc Martinoli, Villeneuve-la-Garenne, both of France

[73] Assignee: Serbio, France

[21] Appl. No.: 768,328

[22] PCT Filed: Dec. 31, 1990

[86] PCT No.: PCT/FR90/00975

§ 371 Date: Oct. 17, 1991

§ 102(e) Date: Oct. 17, 1991

[87] PCT Pub. No.: WO91/12263

PCT Pub. Date: Aug. 22, 1991

[30] Foreign Application Priority Data

Feb. 19, 1990 [FR] France .................. 90 01964

[51] Int. Cl.$^5$ .............. C07K 5/06; C07K 5/08; C07K 5/10; C07K 3/08; C12Q 1/38; C12Q 1/56

[52] U.S. Cl. .................. 530/331; 530/330; 424/1.1; 435/23; 435/24; 435/975; 436/804

[58] Field of Search ............ 514/18, 19; 530/331, 530/330; 424/1.1; 435/23, 24, 975; 436/804

[56] References Cited

U.S. PATENT DOCUMENTS

4,409,140 10/1983 Smith et al. .................. 549/288

FOREIGN PATENT DOCUMENTS

0025190 3/1981 European Pat. Off.
0280610 8/1988 European Pat. Off.
87/00056 1/1987 PCT Int'l Appl.

Primary Examiner—Ronald W. Griffin
Attorney, Agent, or Firm—Ostrolenk, Faber, Gerb & Soffen

[57] ABSTRACT

The new invention relates, by way of novel industrial products, to compounds selected from
(i) the symmetrical amino acids and peptides of the formula $$R-A-B-CO-Q-CO-B-A-R \qquad (I)$$

in which
Q is a polyalkylene glycol residue selected from the polyethylene glycol and polypropylene glycol residues of the formula $$-O[CH(X)CH_2O]_n-$$

in which X is H or Me and n is an integer greater than or equal to 1,
B is a single bond, a monoamino acid residue or a peptide chain comprising from 2 to 9 monoamino acid residues,
A is a basic monoamino acid residue selected from the group consisting of α-amino acid residues containing a basic group on a side-chain, and
R is a labeling means making it possible to develop the enzyme substance to be identified or assayed; and
(ii) their addition salts.

These novel compounds are useful as substrates for the assay of enzymes, especially proteases and peptidases.

21 Claims, No Drawings

SYMMETRICAL BIPEPTIDES CONTAINING A POLYALKYLENE GLYCOL RESIDUE, METHOD OF PREPARATION AND USE IN THE ASSAY OF PROTEASES

FIELD OF THE INVENTION

The present invention relates, by way of novel industrial products, to the bipeptide compounds of formula I below. It further relates to their method of preparation and to their use in the field of the assay of enzymes belonging to the group comprising the proteases and peptidases, in particular as substrates in the field of the quantitative assay of such enzymes, especially the enzymes belonging to the class E.C. 3.4.4 (now the new class "E.C. 3.4.21" as defined in the work "Enzyme Nomenclature", Elsevier Scientific Publishing Company, Amsterdam 1973, pages 238 et seq.).

PRIOR ART

The enzymes belonging to the class referred to above are known to be substances which cleave the amide linkages of the protein or peptide backbone at the carboxyl group of Arg, Lys, Orn and His residues. This cleavage mechanism is well known to those skilled in the art and is amply exemplified in the documents of the prior art cited below.

The currently used substrates for enzymes belonging to said class are essentially tri- or tetrapeptide compounds whose N-terminal end is generally substituted by a blocking group such as benzoyl, benzyloxycarbonyl, t-butoxycarbonyl, t-amyloxycarbonyl, tosyl, acetyl or the like and whose C-terminal end is amidated by an aminated group which can be a radioactive radical or a radical, especially a p-nitroaniline group, capable of imparting coloration or fluorescence before or (preferably) after cleavage. Reference is made in this connection to documents FR-A-2 546 163, FR-A-2 372 798, EP-A-0 004 256, U.S. Pat. No 4,508,644, U.S. Pat. No. 4,448,715, FR-A-2 471 411, FR-A-2 317 280 and FR-A-2 459 226.

It is found that the peptide derivatives known in the prior art have little affinity for water. They have a low solubility or dispersibility in water; consequently, it is sometimes necessary to add an organic solvent to make them usable. The systems comprising mixed solvents are scarcely compatible, in general terms, with biological media: they cause either a decrease in the activity of the substrate or, in certain cases, a deterioration in the enzyme which it is desired to assay. Furthermore, the low affinity of these substrates for water causes a decrease in the sensitivity of the enzyme assay methods.

FR-A-2 546 163 cited above has disclosed a technical solution for improving the solubility of enzyme substrates in water, wherein the peptide contains a polyhydroxycarbonyl group on the N-terminal end.

Also, EP-A-0 025 190 has disclosed a polypeptide compound comprising a polyethylene glycol residue monoetherified by an alkyl group (cf. page 8, lines 6-8), namely the product of the formula

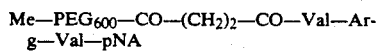

Me—PEG$_{600}$—CO—(CH$_2$)$_2$—CO—Val—Arg—Val—pNA (see page 10, line 35), in which PEG$_{600}$ denotes the polyethylene glycol residue with a molecular weight of the order of about 600.

Finally, EP-A-0 280 160 has disclosed dipeptide substrates whose N-terminal end contains an alkoxycarbonylalkylenecarbonyl radical such as the methoxymalonyl radical.

SOLUTION ACCORDING TO THE INVENTION

According to the invention, a novel technical solution is recommended which differs from that proposed by FR-A-2 546 163, on the one hand, and that envisaged by EP-A-0 025 190, on the other, in that it uses a compound comprising two monoamino acid or peptide chains which are each bonded by their N-terminal end to a divalent polyalkylene glycol group via a carbonyl bridge, CO.

More precisely, this novel technical solution is based on choosing a polyalkylene glycol group belonging to the group consisting of polyethylene glycols and polypropylene glycols, which is bonded to two monoamino acid chains or two peptide chains, each O-terminal end of the polyalkylene glycol residue being joined via a CO group to the N-terminal end of a monoacid or peptide chain so as to impart the solubility or dispersibility in water which is necessary for the sensitivity of enzyme assays. The fact that the polyalkylene glycol residue is bonded to two chains increases the sensitivity of the assay.

SUBJECT OF THE INVENTION

According to the invention, novel compounds are recommended which belong to the group consisting of amino acids and peptides containing an amino acid residue joined to a polyalkylene glycol residue and having a high affinity for water, said compounds, which are structurally different from the peptides known in the prior art, especially as enzyme substrates, being selected from the group consisting of (i) the symmetrical amino acids and peptides of the formula

R—A—B—CO—Q—CO—B—A—R     (I)

in which

Q is a polyalkylene glycol residue selected from the polyethylene glycol and polypropylene glycol residues of the formula

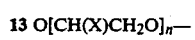

13 O[CH(X)CH$_2$O]$_n$— in which X is H or Me and n is an integer greater than or equal to 1,

B is a single bond, a monoamino acid residue or a peptide chain comprising from 2 to 9 monoamino acid residues, A is a basic monoamino acid residue selected from the group consisting of α-amino acid residues containing a basic group on a side-chain, and R is a labeling means making it possible to develop the enzyme substance to be identified or assayed; and (ii) their addition salts.

ABBREVIATIONS

For convenience, the following abbreviations have been used in the present description:

The Amino Acid Residues

ACC = 1-aminocyclohexane-1-carbonyl
AHX = ε-aminohexanoyl

Aib=2-aminoisobutyryl (or 2-methylalanyl)
Ala=α-alanyl
β-Ala=β-alanyl
Arg=arginyl
Asn=asparaginyl
Asp=α-aspartyl
β-Asp=β-aspartyl
ATC=thiazolidine-4-carbonyl (or thioprolyl)
Aze=azetidine-2-carbonyl
Abu=2-aminobutyryl
4Abu=4-aminobutyryl
CHA=3-cyclohexylalanyl
CHG=α-cyclohexylglycyl
CHT=3-(4-hydroxycyclohexyl)alanyl
Cle=cycloleucyl (or 1-aminocyclopropane-1-carbonyl)
Cys=cysteyl
Dbu=2,4-diaminobutyryl
Gln=glutamyl
Glu=glutaminyl
γ-Glu=γ-glutaminyl
Gly=glycyl
His=histidyl
3Hyp=3-hydroxyprolyl (or 3-hydroxypyrrolidine-2-carbonyl)
4Hyp=4-hydroxyprolyl (or 4-hydroxypyrrolidine-2-carbonyl)
Ile=isoleucyl
Leu=leucyl
Lys=lysyl
MeGly=N-methylglycyl (or sarcosyl)
Met=methionyl
Nle=norleucyl
Nva=norvalyl
Orn=ornithinyl
Phe=phenylalanyl
Phg=phenylglycyl
Pip=pipecolinoyl
Pro=prolyl
Pyr=pyroglutaminyl (or pyrrolidin-2-one-5-carbonyl)
Ser=seryl
Thr=threonyl
Tyr=tyrosyl
Val=valyl The Other Abbreviations Ac=acetyl
AcOH=acetic acid
Adoc=adamantyloxycarbonyl
Aoc=t-amyloxycarbonyl
Boc=t-butoxycarbonyl
Bu=n-butyl
Bop=(benzotriazol-1-yl)oxytris(dimethylamino)phosphonium hexafluorophosphate (alternative nomenclature: CASTRO's reagent) of the formula

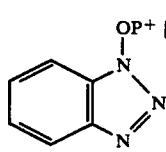

Bz=benzoyl
Bzl=benzyl
Cbo=carbobenzoxy
o-Cl-pNA=o-chloro-p-nitroanilino [or (2-Cl)pNA]
DCCI=dicyclohexylcarbodiimide
DCHU=dicyclohexylurea
DIEA=diisopropylethylamine
DMF=dimethylformamide
Et=ethyl
Et$_3$N=triethylamine
EtO=ethoxy
Fmoc=fluoren-9-ylmethoxycarbonyl
Foc=furfuryloxycarbonyl
HMPT=N,N,N',N',N'',N''-hexamethylphosphorotriamide
HOBT=1-hydroxybenzotriazole
H-TFA=trifluoroacetic acid (or HTFA)
Iboc=isobornyloxycarbonyl
iBu=isobutyl
iPr=isopropyl
Me=methyl
MeO=methoxy
Mor=morpholin-1-yl
MW=molecular weight
OD=optical density
OSu=N-oxysuccinimide or (2,4-dioxopyrrolidin-1-yl)oxy
PAG=polyalkylene glycol
PEG=polyethylene glycol
Ph=phenyl
pH=cologarithm of the concentration of H$^+$ ions
Pi=piperidin-1-yl
pNA=p-nitroanilino or (4-NO$_2$)C$_6$H$_4$NH
PPG=polypropylene glycol
Pr=n-propyl
Py=pyrrolidin-1-yl
RT=room temperature 15°-20° C.)
tBu=t-butyl
TEA=triethanolamine
THF=tetrahydrofuran
TLC=thin layer chromatography
Tos=p-toluenesulfonyl (or tosyl)
Z=benzyloxycarbonyl
Z(p-Cl)=p-chlorobenzyloxycarbonyl
Z(p-OMe)=p-methoxybenzyloxycarbonyl

DETAILED DESCRIPTION OF THE INVENTION

The group Q is a polyalkylene glycol (PAG) residue. It includes polyethylene glycol (PEG) residues when X=H and polypropylene glycol (PPG) residues when X=Me. In the group Q, each O-terminal end is joined to the N-terminal end of one of the two mono-amino acid or peptide chains by a carbonyl group. Advantageously, the PAG residue will have an average molecular weight of between about 60 and about 1000 and preferably of between 200 and 600. Q will be a polyethylene glycol (PEG) residue in preference to a polypropylene glycol (PPG) residue. For the sake of convenience and uniformity, the expressions "polyalkylene glycol residue" and "polyethylene glycol residue" have been used hereafter even when the number n is equal to 1 in formula I.

As indicated above, the group A is the residue of a basic α-monoamino acid. It is derived from a monoamino acid which has a pH greater than 7, i.e. which has an acid group COOH and, in addition to the basic group in the α position, at least one basic sidegroup. Dbu, Arg, Lys, His and Orn residues may be mentioned in particular among the α-amino acid residues which are suitable. The preferred residues A are α-L-amino acid residues, especially L-Arg, L-Lys and L-Orn, the most valuable residue according to the invention being L-Arg.

As indicated above, the group B is a single bond, a monoamino acid residue or a peptide chain containing from 2 to 9 amino acids. The amino acids which are present in the group B can be of any type, especially natural or synthetic. In particular, when B is a monoamino acid residue, said residue will be either a residue devoid of an asymmetric carbon atom (such as, in particular, Aib, Cle, Gly, MeGly and 4Abu) or a residue containing an asymmetric carbon atom and having the L or D configuration, the other amino acid residue or residues of the peptide chain each being an amino acid devoid of an asymmetric carbon atom or an amino acid containing an asymmetric carbon atom and having the L configuration.

When B is a monoamino acid residue, it is derived from a natural or synthetic amino acid which has a pH less than or equal to 7, or from an amino acid which has a pH greater than 7 but which is appropriately substituted so that its basic character is essentially blocked and the pH is less than or equal to 7.

B therefore encompasses:

1) natural or synthetic amino acid residues which comprise a single basic group, 2) natural or synthetic amino acid residues which comprise a single basic group and more than one acid group and in which each acid side-group (not forming part of or not being present in the peptide linkage) is capable of being blocked, especially in the form of an amide or ester, and 3) natural or synthetic amino acid residues which comprise a single acid group and more than one basic group and in which each basic side-group is appropriately substituted so that its basic character is essentially blocked and eliminated.

Of course, the amino acid residues referred to above, which are listed in particular in the abbreviations section above, can contain hydroxyl (OH) or thiol (SH) side-groups which are capable of being blocked, if appropriate, by an ether or ester protecting group.

The residues derived from the following amino acids are particularly suitable for B:

so-called "neutral"non-basic natural amino acids, such as, in particular, Ala, β-Ala, Cys, Gln, 4Hyp, 3Hyp, Leu, Met, Nle, Nva, Phe, Pro, MeGly, Ser, Tyr and Val, where the OH side-group of the 4Hyp, 3Hyp, Ser, Thr and Tyr residues may or may not be protected by an ether or ester protecting group, and where the SH side-group of the Cys residue may or may not be protected by a thioether or thioester protecting group;

acidic natural amino acids, such as, in particular, Asp, β-Asp, Glu and γ-Glu, in which the acid side-group is free or blocked in the form of an amide or ester, especially in the form of the benzyl or t-butyl ester;

initially basic natural amino acids in which the basic side-group or side-groups not forming part of the peptide linkage are blocked by an appropriate acid group which practically eliminates the basic character, such as Adoc, Aoc, Boc, Cbo, Foc, Fmoc, Iboc, Z, Z(p-Cl) and Z(p-OMe) etc., said amino acid residues being especially Arg, Lys, His and Orn residues appropriately blocked by a Cbo group in particular;

so-called "neutral" non-basic synthetic amino acids, such as, in particular, ACC, AHX, Aib, ATC, Aze, Abu, 4Abu, CHA, CHG, CHT (where the OH side-group is protected, if appropriate, in the form of an ether or ester), Cle, Phg, Pip and Pyr; and initially basic synthetic amino acids in which each basic side-group is protected by an appropriate group which substantially eliminates the basic character, especially the Dbu residue, where the basic side-group is blocked by a group such as Cbo.

The following may be mentioned among the synthetic amino acid residues which are also suitable: (i) cycloaliphatic amino acid residues in which the amino group and the carboxyl group are located on the same ring carbon atom (such as the Cle group referred to above) or on two different ring carbon atoms, and (ii) aromatic amino acid residues such as, in particular, o-, m- and p-aminobenzoyl residues, and aralkyl amino acid residues such as, in particular, p-aminobenzylcarbonyl and m-aminobenzylcarbonyl.

Advantageously, the monoamino acid residue of B, according to the invention, will be an α-amino acid residue such as ACC, Aib, Ala, ATC, Asp, Aze, But, CHA, CHG, Cle, Glu, Gly, 4Hyp, 3Hyp, Ile, Leu, Met, Nle, Nva, Phe, Pip, Pro, MeGly, Ser, Thr, Tyr or Val, a β-amino acid residue such as β-Ala, a CHT, 4Hyp, 3Hyp, Ser, Thr or Tyr residue in which the OH side-group is protected in the form of an ether or ester, or an Asp or Glu residue in which the OH group of the carboxylic acid side-group has been replaced with a group $OR_3$, $NH_2$, $NHR_4$ or $NR_4R_5$, in which $R_3$ is $C_1$–$C_4$ alkyl (preferably Me, Et, iBu, Bu), $C_1$–$C_4$ hydroxyalkyl (preferably $CH_2CH_2OH$), $C_3$–$C_6$ cycloalkyl (such as cyclopropyl, cyclopentyl or cyclohexyl) or ω-aminoalkyl [in which the alkyl fragment is $C_2$–$C_4$ and in which the amino group can be monoalkylated ($NHR_4$), dialkylated ($NR_4R_5$) or included in a ring ($NR_4R_5$ = heterocyclic group)] and $R_4$ and $R_5$, which are identical or different, are each a $C_1$–$C_4$ alkyl group, it being possible for $R_4$ and $R_5$, taken together, to form, with the nitrogen atom to which they are bonded, an N-heterocyclic group selected from the group consisting of pyrrolidino, piperidino, morpholino, thiomorpholino, piperazino, 4-(2-hydroxyethyl)piperazino, 4-methylpiperazino, 4-(4-chlorophenyl)piperazino and hexamethyleneimino groups.

The monoamino acid residue B therefore includes amino acid residues, such as Aib, β-Ala, Cle, Gly, MeGly and 4Abu, which are devoid of an asymmetric carbon atom, and amino acid residues which contain an asymmetric carbon atom.

When the only amino acid present in B contains an asymmetric carbon atom, the residue of said amino acid will preferably have the L configuration, experience having shown that the tripeptides of formula I in which B is a monoamino acid residue having the D configuration are generally less active as substrates.

The monoamino acid group B will preferably be selected from the group consisting of (i) Aib, L-Ala, β-Ala, L-ATC, L-Aze, L-Abu, L-CHA, L-CHG, L-CHT, Cle, Gly, L-4Hyp, L-3Hyp, L-Asp, L-Glu, L-Ile, L-Leu, L-Nle, L-Nva, L-Phe, L-Pip, L-Pro, MeGly, L-Ser, L-Thr, L-Tyr and L-Val residues, (ii) L-CHT, L-4Hyp, L-3Hyp, L-Ser, L-Thr and L-Tyr residues in which the OH side-group is protected in the form of an ester or ether group, (iii) L-Arg, L-Lys, L-His, L-Orn and L-Dbu residues in which the basic side-group is substituted by an appropriate group for substantially eliminating the basic character of said side-group, said appropriate group being derived from an acid group, especially Cbo, and (iv) L-Asp or L-Glu residues in which the carboxylic acid side-group is esterified or amidated.

When B is a peptide group containing from 2 to 9 amino acid residues, each of the amino acids of the peptide chain will be selected from the amino acid residues listed above where group B=monoamino acid. Preferably, the peptide chain made up of B will only contain α-amino acid residues in this case.

The amino acid containing the N-terminal end of said peptide chain which is bonded to the group Q via a carbonyl bridge will also preferably be an α-amino acid residue selected from the group consisting of (i) α-amino acid residues devoid of an asymmetric carbon atom, such as Aib, Cle and Gly, and (ii) α-amino acid residues containing an asymmetric carbon atom and having the D or L configuration, the other amino acid residue or residues of said peptide chain preferably being (a) Aib, Cle or Gly, or (b) one or more α-amino acid residues having the L configuration.

Furthermore, when B is a peptide chain, said peptide chain will advantageously contain 2 or 3 amino acids, i.e. the compounds of formula I will then be bis(tripeptides) or bis(tetrapeptides).

Moreover, when B is a peptide chain containing 2 to 3 amino acid residues, it is recommended in particular that the amino acid residue in the 2 position, i.e. the one directly bonded to the amino acid residue containing the N-terminal end of B-A, should be Asp or Glu, it being possible, if appropriate, for the carboxyl side-group of each Asp or Glu residue to be esterified or amidated, as indicated above, in order to form compounds of formula I which are particularly useful in the field of the determination of the Factor Xa involved in hemostasis.

The labeling means R is well known in the art of biological and microbiological assays; reference is made in this connection to the prior art cited above and especially document U.S. Pat. No. 4,448,715. Said labeling means will preferably be selected from the group consisting of the aminated groups NH-R' which (i) induce a color change, (ii) induce a change in fluorescence, or (iii) contain at least one radioactive element (for example an anilino or benzylamino group labeled with a $^{14}$C or $^3$H radioisotope). Any amino group NH-R' which gives, during or after the enzymic reaction, a signal capable of being amplified for detection (for example by measurement of the optical density at a given wavelength, or by measurement of the radioactivity) is suitable for the purposes of the invention. The amount of product H-R obtained by cleavage in the enzymic hydrolysis is proportional to the amount of enzyme used. Said amount of H-R can be determined by photometry, spectrophotometry, fluorospectrophotometry or electrochemistry.

The group R which is recommended according to the invention is a chromogenic group, typically a nitrophenylamino group (in which the phenyl radical is capable of being substituted by a group COOH, F, Cl, Br, $CH_3$, $OCH_3$, CN, $CF_3$ and/or $SO_3H$), or a fluorogenic group, typically a naphthylamino group (in which the naphthyl radical is capable of being substituted by a group $OCH_3$, COOH, $SO_3H$ or $CH_3$), and 4-methylcoumaryl-7-amino, 4-trifluoromethylcoumaryl-7-amino and analogous groups.

The following may be mentioned in particular among the chromogenic and fluorogenic aminated groups which are suitable according to the invention: p-nitroanilino (abbreviated to pNA), 2-carboxy-4-nitroanilino and 3-carboxy-4-nitroanilino, 2-halogeno-4-nitroanilino and 3-halogeno-4-nitroanilino (in which the halogen is F, Cl or Br), 2-methoxy-5-methyl-4-nitroanilino, 2-hydroxysulfonyl-4-nitroanilino, 4-trifluoromethyl-2-nitroanilino, 4-trifluoromethyl-3-nitroanilino, 4-cyano-2-nitroanilino, naphthyl-2-amino, 4-hydroxysulfonylnaphthyl-1-amino, quinolylamino, nitroquinolylamino and the like.

The preferred group R according to the invention is a chromogenic group, namely on the one hand pNA, which is generally suitable for the quantitative determination of the proteolytic enzymes referred to above and is particularly suitable for the determination of Factor Xa, protein C and/or plasmin, and on the other hand analogous groups in which the phenyl ring of pNA is substituted in the 2 or 3 position, said groups having the formula

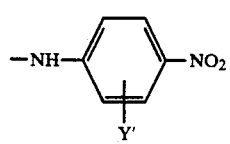

in which Y' is Br, Cl, F, $CF_3$, COOH, COOW, $CONH_2$, CONHW, $CONW_2$, $CONH(CH_2)_mNMe_2$, OH or OW, in which W is a $C_3$-$C_6$ alkyl, $C_6$-$C_{10}$ aryl, $C_7$-$C_{11}$ aralkyl or $C_3$-$C_8$ alicyclic group and m is an integer having a value of to 10.

Such groups of formula II in which the phenyl ring of the pNA group is substituted are described especially in document EP-A-0 110 306.

The addition salts according to the invention are essentially acid addition salts obtained by reacting a compound of formula I with a mineral or organic acid.

The best mode of carrying out the invention consists in using, as the substrate, a symmetrical bipeptide compound selected from the group consisting of (i) the compounds of the formula

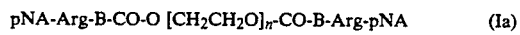

in which

B is a single bond; an Aib, Cle or Gly residue or a monoamino acid residue having the L configuration; or a di- or tri-peptide residue in which the amino acid residue containing the N-terminal end of the peptide chain which is bonded to the carbonyl bridge, CO, is Aib, Cle or Gly or has the L or D configuration, the other amino acid residue or residues being Aib, Cle or Gly or having the L configuration; and n is an integer greater than or equal to 1, such that the average molecular weight of the group $O[CH_2CH_2O]_n$ is between about 60 and about 600 and preferably between 200 and 400; and (ii) their addition salts.

From a practical point of view, within the framework of the best mode of carrying out the invention, it is particularly advantageous that the average molecular weight of the group $O[CH_2CH_2O]_n$ should be of the order of 200–400, i.e. that the group $O[CH_2CH_2O]_n$ should be derived from a PEG compound having a molecular weight of 200–400, on the one hand, and that the group B should be a di- or tri-peptide residue, on the other.

Without implying a limitation, a number of peptide compounds according to the invention have been collated in Table I below, the most valuable being in particular:

(a) PEG$_{200}$(CO-Gly-L-Pro-L-Arg-pNA)$_2$,
(b) PEG$_{600}$(CO-Gly-L-Pro-L-Arg-pNA)$_2$,
(c) PEG$_{200}$(CO-D-Glu(OBzl)-L-Pro-L-Arg-pNA)$_2$,
(d) PEG$_{200}$(CO-D-Nle-L-CHA-L-Arg-pNA)$_2$,
(e) PEG$_{200}$(CO-D-Leu-Gly-L-Arg-pNA)$_2$,
(f) PEG$_{200}$(CO-D-CHA-Gly-L-Arg-pNA)$_2$,
(g) PEG$_{300}$(CO-D-Leu-Gly-L-Arg-pNA)$_2$,
(h) PEG$_{400}$(CO-D-Leu-Gly-L-Arg-pNA)$_2$,
(i) PEG$_{200}$(CO-D-Nle-Gly-L-Arg-pNA)$_2$ and
(j) their addition salts.

Like the substrates known in the prior art, the symmetrical compounds of formula I or Ia and their addition salts according to the invention give, on enzymic hydrolysis, a quantity of H-R which is proportional to the amount of enzyme present in the test sample. On the other hand, the compounds according to the invention have different enzymic hydrolysis kinetics from said substrates known in the prior art.

TABLE I

| Product | pNA—A—B—CO—Q—CO—B—A—pNA.xHAo | | | |
|---|---|---|---|---|
| | Q | B(1) | A | xHAo |
| Ex. 1 | PEG$_{200}$ | Gly-L-Pro | L-Arg | 2H-TFA |
| Ex. 2 | PEG$_{200}$ | Gly-L-Pro | L-Arg | 2AcOH |
| Ex. 3 | PEG$_{600}$ | Gly-L-Pro | L-Arg | 2AcOH |
| Ex. 4 | PEG$_{200}$ | D-Glu(OBzl)-L-Pro | L-Arg | 2AcOH |
| Ex. 5 | PEG$_{200}$ | D-Nle-L-CHA | L-Arg | 2AcOH |
| Ex. 6 | PEG$_{200}$ | D-Leu—Gly | L-Arg | 2AcOH |
| Ex. 7 | PEG$_{200}$ | D-CHA—Gly | L-Arg | 2AcOH |
| Ex. 8 | PEG$_{300}$ | D-Leu—Gly | L-Arg | 2AcOH |
| Ex. 9 | PEG$_{400}$ | D-Leu—Gly | L-Arg | 2AcOH |
| Ex. 10 | PEG$_{200}$ | D-Nle—Gly | L-Arg | 2AcOH |
| Ex. 11 | PEG$_{400}$ | Gly-L-Pro | L-Arg | 2AcOH |
| Ex. 12 | PEG$_{200}$ | D-CHA-L-3Hyp | L-Arg | 2AcOH |
| Ex. 13 | PEG$_{200}$ | Gly-L-Pip | L-Arg | 2AcOH |
| Ex. 14 | PEG$_{400}$ | Gly-L-Pip | L-Arg | 2AcOH |
| Ex. 15 | PEG$_{200}$ | D-Lys($\epsilon$-Cbo)-L-ATC | L-Arg | 2AcOH |
| Ex. 16 | PEG$_{400}$ | D-CHA-L-Nle | L-Arg | 2AcOH |
| Ex. 17 | PEG$_{200}$ | D-Ala-L-Nva | L-Arg | 2AcOH |
| Ex. 18 | PEG$_{200}$ | D-Thr(Bzl)-L-AHX | L-Lys | 2AcOH |
| Ex. 19 | PEG$_{400}$ | D-Pro-L-Pro | L-Arg | 2AcOH |
| Ex. 20 | PEG$_{200}$ | D-Lys($\epsilon$-Cbo)-L-Phe | L-Arg | 2AcOH |
| Ex. 21 | PEG$_{400}$ | Gly-L-Phe | L-His | 2AcOH |
| Ex. 22 | PEG$_{200}$ | D-But-L-Leu | L-Arg | 2AcOH |
| Ex. 23 | PEG$_{200}$ | D-Lys($\epsilon$-Cbo)-L-Leu | L-Arg | 2AcOH |
| Ex. 24 | PEG$_{400}$ | D-Ser(Bzl)-L-Leu | L-Arg | 2AcOH |
| Ex. 25 | PEG$_{200}$ | D-Ala-L-4Hyp | L-Arg | 2AcOH |
| Ex. 26 | PEG$_{200}$ | D-CHA-L-Abu | L-Arg | 2AcOH |
| Ex. 27 | PEG$_{400}$ | D-Leu-L-Pro | L-Arg | 2AcOH |
| Ex. 28 | PEG$_{400}$ | D-But-L-CHA | L-Arg | 2AcOH |
| Ex. 29 | PEG$_{200}$ | D-Lys($\epsilon$-Cbo)-L-Pro | L-Arg | 2AcOH |
| Ex. 30 | PEG$_{200}$ | D-Nle-L-CHA | L-Lys | 2AcOH |
| Ex. 31 | PEG$_{400}$ | D-Pro-L-Pro | L-Orn | 2AcOH |
| Ex. 32 | PEG$_{400}$ | D-Leu—Gly | L-Orn | 2AcOH |
| Ex. 33 | PEG$_{400}$ | D-Glu—Gly-L-Leu | L-Arg | 2AcOH |
| Ex. 34 | PEG$_{200}$ | D-Leu-L-Leu-L-CHA | L-Arg | 2AcOH |
| Ex. 35 | PEG$_{200}$ | D-Thr(Bzl)-L-Leu-L-CHA | L-Arg | 2AcOH |
| Ex. 36 | PEG$_{400}$ | D-CHA—Gly | L-Arg | 2AcOH |
| Ex. 37 | PEG$_{400}$ | D-Nle—Gly | L-Arg | 2AcOH |
| Ex. 38 | PEG$_{400}$ | D-CHG—Gly | L-Arg | 2AcOH |
| Ex. 39 | PEG$_{600}$ | D-CHA—Gly | L-Arg | 2AcOH |
| Ex. 40 | PEG$_{400}$ | D-CHT—Gly | L-Arg | 2AcOH |
| Ex. 41 | PEG$_{400}$ | D-Nva—Gly | L-Arg | 2AcOH |
| Ex. 42 | PEG$_{400}$ | D-Val—Gly | L-Arg | 2AcOH |
| Ex. 43 | PEG$_{400}$ | D-Ile-L-Glu—Gly | L-Arg | 2AcOH |
| Ex. 44 | PEG$_{400}$ | D-Ile-L-Glu(OMe)—Gly | L-Arg | 2AcOH |
| Ex. 45 | PEG$_{400}$ | D-Ile-L-Glu(Py)—Gly | L-Arg | 2AcOH |
| Ex. 46 | PEG$_{400}$ | D-Ile-L-Asp(Mor)—Gly | L-Arg | 2AcOH |
| Ex. 47 | PEG$_{400}$ | D-Phe—Gly | L-Arg | 2AcOH |
| Ex. 48 | PEG$_{400}$ | D-Lys($\omega$-Cbo)—Gly | L-Arg | 2AcOH |
| Ex. 49 | PEG$_{400}$ | D-CHG-L-Glu(OMe)—Gly | L-Arg | 2AcOH |
| Ex. 50 | PEG$_{400}$ | D-Leu—MeGly | L-Arg | 2AcOH |
| Ex. 51 | PEG$_{400}$ | D-Nle-L-Glu(OiPr)—Gly | L-Arg | 2AcOH |
| Ex. 52 | PEG$_{400}$ | D-Ile-L-Glu(OtBu)—Gly | L-Arg | 2AcOH |
| Ex. 53 | PEG$_{200}$ | D-CHG—Aib-L-CHA | L-Arg | 2AcOH |

TABLE I-continued

| Product | pNA—A—B—CO—Q—CO—B—A—pNA.xHAo | | | |
|---|---|---|---|---|
| | Q | B(1) | A | xHAo |
| Ex. 54 | PEG$_{400}$ | D-Leu—Cle-L-Pro | L-Arg | 2AcOH |
| Ex. 55 | PEG$_{400}$ | D-Pro—Cle-L-Leu | L-Arg | 2AcOH |
| Ex. 56 | PEG$_{400}$ | D-Nle—Aib-L-Pro | L-Arg | 2AcOH |
| Ex. 57 | PEG$_{400}$ | D-Nva—Gly-L-Pro | L-His | 2AcOH |
| Ex. 58 | PEG$_{200}$ | Aib-L-CHG-L-Pro | L-Arg | 2AcOH |
| Ex. 59 | PEG$_{200}$ | Aib-L-Lys($\epsilon$-Cbo)-L-Pro | L-Arg | 2AcOH |
| Ex. 60 | PEG$_{200}$ | Gly-L-Leu-L-CHA | L-Arg | 2AcOH |
| Ex. 61 | PEG$_{400}$ | Gly-L-Thr(Bzl)-L-Abu | L-Arg | 2AcOH |
| Ex. 62 | PEG$_{400}$ | D-Leu-L-Asp(Pi)—Gly | L-Arg | 2AcOH |
| Ex. 63 | PEG$_{200}$ | D-Val-L-Glu(Pi)—Gly | L-Arg | 2AcOH |
| Ex. 64 | PEG$_{60}$ | D-Leu—Gly | L-Arg | 2AcOH |
| Ex. 65 | PEG$_{60}$ | D-Nle—Gly | L-Arg | 2AcOH |
| Ex. 66 | PEG$_{100}$ | D-Leu—Gly | L-Arg | 2AcOH |
| Ex. 67 | PEG$_{150}$ | D-Leu—Gly | L-Arg | 2AcOH |

Notes
(i) The first amino acid mentioned is bonded by its N-terminal end to the carbonyl bridge, CO.
Comparison products:
CP 1: MeSO$_2$-D-Leu—Gly-L-Arg-pNA.AcOH
CP 2: H-D-CHG-L-Abu-L-Arg-pNA.2AcOH
CP 3: H-D-Abu-L-CHA-L-Arg-pNA.2AcOH The compounds of formula I according to the invention can be prepared in accordance with a method known per se by the application of conventional reaction mechanisms.

The method which is recommended here consists in reacting an amino acid or peptide compound of the formula $$H-B-A-R \qquad (IV)$$

in which B, A and R are defined as indicated above, with a polyalkylene glycol dihalogenoformate of the formula $$Hal-CO-Q-CO-Hal \qquad (V)$$

in which Hal is a halogen atom, especially F, Cl or Br and preferably Cl, and Q is defined as indicated above, according to the reaction $$2(H-B-A-R)+Hal-CO-Q-CO-Hal \rightarrow I$$

The starting compounds of formulae IV and V are obtained by conventional methods well known to those skilled in the art. In particular, when B is other than a single bond, the compound IV is obtained by one of the customary methods of peptide synthesis.

Advantageously, 2 mol of IV will be reacted with 1 to 1.3 mol (preferably 1 to 1.1 mol) of V in an inert solvent (especially DMF or THF) at a temperature of between 0° and 40° C. for at least 0.25 h, in the presence of a proton acceptor, especially a tertiary amine such as Et$_3$N or DIEA, which is also present as a cosolvent for the reaction medium. It will be preferred to use an excess of tertiary amine relative to stoichiometric conditions, especially in a molar ratio tertiary amine/compound IV of 1.7/1 to 2.6/1 and preferably of 2/1 to 3.1/1.

The tripeptide compounds of formula I and their addition salts are useful in the determination of the enzymes involved in hemostasis. In particular, they constitute specific substrates for Factor Xa, plasmin or thrombin. The recommended method of determining these enzymes comprises bringing a given amount of a tripeptide of formula I or of one of its addition salts (at a concentration of the order of 10 mg/ml) into contact, in an appropriate aqueous liquid medium such as a buffered isotonic solution, with a test sample (diluted if appropriate) which may contain the target enzyme, for at least 0.5 h at a temperature of between RT and 40° C., especially 37° C.

The activity of the tripeptides according to the invention towards enzymes involved in hemostasis was determined by conventional methods such as those described in EP-A-0 280 160 (see page 14), the hydrolysis rate being assessed by the variation in optical density with time ($\Delta$OD/min). The results obtained have been collated in Table II below, where the activity of reference products (CP 1 to CP 3) is specified as being equal to 100% for the sake of convenience.

Further advantages and characteristics of the invention will be understood more clearly from the following description of preparatory examples and results of comparative tests. Of course, these data as a whole do not in any way imply a limitation but are given by way of illustration.

PREPARATION I

Preparation of
$PEG_{200}$(D-Leu-Gly-L-Arg-pNA)$_2$.2AcOH (Example 5)

a) Z-L-Arg-pNA.HCl 344 g (1 mol) of Z-L-Arg-OH.HCl are dissolved in anhydrous HMPT (freshly distilled and dried over a molecular sieve) at RT and 139 ml (1 mol) of Et$_3$N are then added at RT, with stirring. 328 g (2 mol) of p-nitrophenyl isocyanate are added to the resulting solution. The resulting reaction medium is stirred for 24 h at RT and then evaporated under vacuum and the residue is taken up with the minimum amount of AcOH and then diluted with AcOEt. The resulting solution is subsequently extracted successively three times with small amounts of 0.5M NaHCO$_3$, three times with a solution of KHSO$_4$ at 50 g/l and then several times with H$_2$O semisaturated with NaCl. The organic phase is then dried over anhydrous sodium sulfate. After filtration (removal of Na$_2$SO$_4$), the solvent is evaporated off and the evaporation residue is recrystallized from an AcOEt/MeOMe mixture (3/7 v/v) to give 350 g of the expected product in the form of a white powder.

M.p. = 128°–130° C.

Analysis (TLC on silica gel):
Rf=0.5 in AcOEt/pyridine/AcOH/H$_2$O (20/4.5/3/1 v/v);
Rf=0.69 in CHCl$_3$/MeOH/AcOH (5/3/1 v/v).

b) H-L-Arg-pNA.2HBr 100 g (0.215 mol) of Z-L-Arg-pNA.HCl are charged into a glass/Teflon apparatus. 800 ml of glacial AcOH, 200 ml of anisole and 1000 ml of a solution of HBr in glacial AcOH are added successively under an inert atmosphere (stream of nitrogen). The reaction is left to proceed for 1 h at RT under a nitrogen atmosphere. After this time has elapsed, the reaction mixture, which has become homogeneous during the deprotection, is precipitated in 20 l of ether (MeOMe or EtOEt). After decantation, the supernatant is discarded and the precipitate is washed several times with ether. The precipitate is collected by filtration and dried under vacuum over KOH for 24 h to give 94.2 g (yield: 96%) of the expected product.

Analysis (TLC on silica gel): Rf=0.04 in AcOEt/pyridine/AcOH/H$_2$O (20/4.5/3/1.5 v/v); Rf=0.38 in BuOH/AcOH/H$_2$O (3/1/1 v/v).

c) Boc-Gly-L-Arg-pNA.HBr 1 g (2.19 mmol) of H-L-Arg-pNA.2HBr is dissolved in 10 ml of DMF, and 0.854 ml (6.57 mmol) of DIEA is then added. In another vessel, a solution of 384 mg (2.19 mmol) of Boc-Gly-OH in 5 ml of DMF is neutralized with 0.285 ml of DIEA. The two solutions obtained in this way are mixed and 970 mg of Bop are added to the resulting medium, the latter being kept at RT; also, the pH is kept at a value of between 7 and 8 by the addition of small portions of DIEA throughout the reaction. After one hour, the reaction has completely finished and the reaction medium is evaporated to dryness under vacuum; the evaporation residue is taken up with an AcOEt/MeOH mixture and extracted with a 0.5M aqueous solution of NaHCO$_3$. The organic phase is dried over sodium sulfate, concentrated under vacuum and then precipitated in ether (MeOMe or EtOEt) to give 874 mg (yield: 75%) of the expected product.

Analysis (TLC on silica gel): Rf=0.53 in CHCl$_3$/MeOH/AcOH (10/3/1 v/v).

d) H-Gly-L-Arg-pNA.2H-TFA 874 mg (1.64 mmol) of Boc-Gly-L-Arg-pNA.HBr are charged into a reactor and 6.6 ml of CH$_2$Cl$_2$ and 6.6 ml of H-TFA are then added successively. After a reaction time of 0.25 h at RT, the reaction mixture is precipitated directly in ether. A flaky white precipitate is formed which is filtered off and dried to give 910 mg (yield: 96%) of the expected product.

Analysis (TLC on silica gel): Rf=0.09 in CHCl$_3$/MeOH/AcOH (5/3 1 v/v).

e) Boc-D-Leu-Gly-L-Arg-pNA.H-TFA

Following the procedures of Preparation Ic, a reaction mixture comprising (i) 910 mg (1.57 mmol) of H-Gly-L-Arg-pNA.2H-TFA, (ii) 363 mg (1.57 mmol) of Boc-D-Leu-OH, (iii) 1.2 ml of DIEA and (iv) 695 mg (1.57 mmol) of Bop is reacted in DMF and the reaction mixture is kept at RT for 2 h, with stirring. After evaporation to dryness under vacuum, the evaporation residue is chromatographed on silica gel using a CHCl$_3$/MeOH/AcOH gradient (20/3/1 to 10/3/1 v/v) as the eluent. The homogeneous fractions collected are pooled and the eluent is evaporated off. Lyophilization gives 785 mg (yield: 80%) of the expected product in pure form.

Analysis (TLC on silica gel): Rf=0.33 in CHCl$_3$/MeOH/AcOH (10/3/1 v/v).

f) H-D-Leu-Gly-L-Arg-pNA.2H-TFA 785 mg (1.25 mmol) of Boc-D-Leu-Gly-L-Arg-pNA.H-TFA, obtained according to Preparation Ie, are reacted with 5 ml of CH$_2$Cl$_2$ and 5 ml of H-TFA at RT. After 0.25 h, the reaction mixture is precipitated directly in ether to give a white precipitate, which is filtered off, washed with ether and dried. 779 mg (yield: 90%) of the expected product are collected.

Analysis (TLC on silica gel): Rf=0.2 in CHCl$_3$/MeOH/AcOH (5/3/1 v/v).

g) $PEG_{200}$(D-Leu-Gly-L-Arg-pNA)$_2$.2AcOH 15 ml of DMF and 0.345 ml (2.47 mmol) of Et$_3$N are added to 779 mg (1.12 mmol) of H-D-Leu-Gly-L-Arg-pNA.2H-TFA, obtained as indicated above. The resulting mixture is cooled in ice, with stirring. 182 mg (0.563 mmol) of $PEG_{200}$ dichloroformate [obtained according to Preparation VIII below and having the structural formula Cl—CO—O(CH$_2$CH$_2$O)$_n$—CO—Cl, in which n is such that the MW of the fragment O(CH$_2$CH$_2$O)$_n$ has a value of about 200] in 5 ml of DMF are then added dropwise. The resulting reaction mixture is then allowed to warm up slowly to RT over 2 h. It is filtered to remove the triethylammonium salt which has formed, and the filtrate is evaporated. The evaporation residue is chromatographed on an ion exchange resin (AMBERLITE® IRA 4015) using an MeOH/H$_2$O mixture (3/2 v/v) as the eluent. The homogeneous fractions obtained are pooled. Evaporation followed by lyophilization gives 460 mg (yield: 63%) of the expected product.

Analysis (TLC on silica gel): Rf=0.34 in CHCl$_3$/MeOH/AcOH (5/3/1 v/v).

PREPARATION II

Preparation of PEG$_{300}$(D-Leu-Gly-L-Arg-pNA)$_2$.2AcOH (Example 8)

The procedure given in Preparation Ig is followed except that the PEG$_{200}$ dichloroformate is replaced with PEG$_{300}$ dichloroformate to give the expected product.

PREPARATION III

Preparation of PEG$_{400}$(D-Leu-Gly-L-Arg-pNA)$_2$.2AcOH (Example 9)

The procedure given in Preparation Ig is followed except that the PEG$_{200}$ dichloroformate is replaced with PEG$_{400}$ dichloroformate to give the expected product.

PREPARATION IV

Preparation of PEG$_{200}$(D-Nle-Gly-L-Arg-pNA)$_2$.2AcOH (Example 10)

The procedure given in Preparation I is followed except that the amino acid of the formula Boc-D-Leu-OH is replaced in step Ie with the amino acid of the formula Boc-D-Nle-OH to give the expected product.

PREPARATION V

Preparation of PEG$_{200}$(D-Nle-L-CHA-L-Arg-pNA)$_2$.2AcOH (Example 5)

The procedure given in Preparation I is followed except that the Boc-Gly-OH is replaced in step Ic with Boc-L-CHA-OH and the Boc-D-Leu-OH is replaced in step Ie with the amino acid of the formula Boc-D-Nle-OH to give the expected product.

PREPARATION VI

Preparation of PEG$_{200}$(D-Gly-L-Pro-L-Arg-pNA).2AcOH (Example 2)

a) Z-L-Arg-pNA.HCl 100 g (0.724 mol) of H-pNA are dissolved in 1.5 l of pyridine. The stirred mixture is cooled to −20° C. 64 ml (0.724 mol) of PCl$_3$, cooled to −20° C. beforehand, are added dropwise and the reaction mixture is kept at −20° C. for 1 h. 223 g of Z-L-Arg-OH are then added, the temperature being kept at −20° C. for 1 h, after which the reaction mixture is allowed to warm up to room temperature, which is maintained for 12 h. The resulting reaction mixture is transferred into 10 liters of iced water and the supernatant precipitate is filtered off and then taken up with an AcOH/AcOEt mixture and washed successively (3 times) with a 0.5M aqueous solution of NaHCO$_3$, an aqueous solution of KHSO$_4$ at 50 g/l and then water semisaturated with NaCl. The organic phase is dried over Na$_2$SO$_4$ and then evaporated and concentrated. The resulting concentrate is chromatographed on a column of silica using a CHCl$_3$/MeOH/AcOH gradient system (20/3/1 to 5/3/1 v/v). The homogeneous fractions are pooled, evaporated and precipitated in ether to give 222 g (yield: 66%) of the expected product. M.p.=128°–130° C.

Analysis (TLC on silica gel): Rf=0.76 in CHCl$_3$/MeOH/AcOH (5/3/1 v/v); Rf=0.2 in CHCl$_3$/MeOH/AcOH (20/3/1 v/v).

b) H-L-Arg-pNA.2HBr

The procedure indicated in Preparation Ib is followed.

c) Boc-Gly-L-Pro-OH 1.4 ml (11 mmol) of N-methylmorpholine are added to 1.15 g (10 mmol) of proline in 50 ml of DMF. The mixture is cooled with an ice bath, 3.06 g (10 mmol) of Boc-Gly-OSu are then added and the pH is adjusted to between 6 and 7 throughout the reaction (14 h) by successive additions of small amounts of N-methylmorpholine (this substance is used as a proton acceptor). The DMF is evaporated off and the evaporation residue is taken up with AcOEt; after precipitation in petroleum ether and then filtration, the expected product is collected.

Analysis (TLC on silica gel): Rf=0.53 in BuOH-/AcOH/H$_2$O (3/1/1 v/v); Rf=0.42 in AcOEt/-pyridine/AcOH/H$_2$O (20/4.5/3/1.5 v/v).

d) Boc-Gly-L-Pro-L-Arg-pNA.HBr 1.35 ml of Et$_3$N are added to 4 g (8.8 mmol) of H-L-Arg-pNA.2HBr in 25 ml of DMF. The mixture is cooled with an ice bath and 2.38 g of the dipeptide Boc-Gly-L-Pro-OH, 2.67 g (17.5 mmol) of HOBT and 2.7 g (about 3.15 mmol) of DCCI are then added successively, the pH being adjusted to between 6 and 7 by the addition of Et$_3$N. The reaction medium is stirred at RT for 12 h. It is then filtered (to remove the DCHU formed) and the filtrate is evaporated under vacuum. Precipitation with EtOEt gives a white precipitate, which is taken up with the minimum amount of CHCl$_3$/MeOH/AcOH (8/3/1 v/v). The resulting solution is chromatographed on silica gel using the same solvent system. The homogeneous fractions obtained are recovered and evaporated and lyophilization gives 4.7 g (yield: 85%) of the expected product.

Analysis (TLC on silica gel): Rf=0.64 in BuOH-/AcOH/H$_2$O (3/1/1 v/v); Rf=0.76 in CHCl$_3$/MeOH-/AcOH (5/3/1 v/v).

e) H-Gly-L-Pro-L-Arg-pNA.2H-TFA

The procedure indicated in Preparation If is followed except that the Boc-D-Leu-Gly-L-Arg-pNA.H-TFA is replaced with 4.7 g of Boc-Gly-L-Pro-L-Arg-pNA.HBr to give 5 g of the expected product after precipitation in ether.

Analysis (TLC on silica gel): Rf=0.12 in CHCl$_3$/MeOH/AcOH (5/3/1 v/v)

f) PEG$_{200}$(Gly-L-Pro-L-Arg-pNA)$_2$.2AcOH

Starting from H-Gly-L-Pro-L-Arg-pNA.2H-TFA, the expected product is obtained by the procedures described in Preparation If.

PREPARATION VII

Preparation of
PEG$_{200}$(D-Glu(OBzl)-L-Pro-L-Arg-pNA)$_2$.2AcOH
(Example 4)

The procedure indicated in Preparation VI is followed except that the Boc-Gly-OSu is replaced in step VIc with Boc-D-Glu(OBzl)-OSu to give the expected product.

PREPARATION VIII

Preparation of PEG$_{200}$ dichloroformate 1 g (5 mmol) of PEG$_{200}$ and 1.4 ml (10 mmol) of Et$_3$N dissolved in THF are introduced dropwise by means of a dropping funnel into a reactor containing phosgene, kept at $-30°$ C., so that the phosgene is always in large excess relative to the diol. The mixture is stirred for 2 h at $-30°$ C. and then allowed to warm up to RT. The excess phosgene is totally swept away with a stream of nitrogen, the operation lasting several hours in order to remove said phosgene. The resulting reaction mixture is then evaporated under vacuum to give 1.59 g (yield: 98%) of the expected product in the form of a viscous liquid.

Analysis (IR spectrum):
disappearance of the alcohol bands at 3300 cm$^{-1}$;
appearance of the chloroformate bands at 1776 and 1152 cm$^{-1}$.

The dichloroformates of the other PEGs are also obtained by this method.

COMPARATIVE TESTS

Table II below summarizes the results of the comparative tests which were carried out at equimolar doses with the products of the invention and with standard substances, whose activity was taken as being equal to 100%.

TABLE II

| | ACTIVITIES | | |
|---|---|---|---|
| Product | Xa | Thrombin | Plasmin |
| Ex. 2 | 6% | 34% | 130% |
| Ex. 3 | 10% | 50% | 122% |
| Ex. 4 | 11% | 45% | 289% |
| Ex. 5 | 20% | 110% | 15% |
| Ex. 6 | 105% | 23% | 188% |
| Ex. 7 | 45% | 21% | 112% |
| Ex. 8 | 60% | 25% | 150% |
| Ex. 9 | 74% | 34% | 165% |
| CP 1 | 100% | 18% | 30% |
| CP 2 | 14% | 100% | 77% |
| CP 3 | 14% | 10% | 100% |

Said results show that the compounds according to the invention of Ex. 2–Ex. 4 and Ex. 6–Ex. 9 are more sensitive than the reference substrate CP 3 towards plasmin, and that the product of Ex. 5 is more sensitive than the reference substrate CP 1 towards thrombin. Furthermore, the product of Example 6 can be used to determine Factor Xa when a plasmin inhibitor is introduced into the test sample.

Finally, an assay kit for the determination of enzymes involved in hemostasis, especially plasmin, is recommended according to the invention, said kit containing at least one peptide selected from the group consisting of the compounds of formula I and their addition salts according to the invention and, if appropriate, standard samples of enzymes and of buffered dilution media.

What is claimed is:

1. A compound of the formula $$R-A-B-CO-Q-CO-B-A-R \quad (I)$$

in which

Q is a polyalkylene glycol residue of the formula $$-O[CH(X)CH_2O]_n-$$

in which X is H or Me and n is an integer greater than or equal to 1,

B is a single bond, a non-basic monoamino acid residue or a peptide chain having 2 to 9 monoamino acid residues, A is a basic mono α-amino acid residue containing a basic group on a side-chain, and R is a label; and the acid solution salts thereof.

2. A compound according to claim 1 wherein Q is a polyethylene glycol residue of the formula $-O[CH_2CH_2O]_n-$ having an average molecular weight of 60–1000.

3. A compound according to claim 2 wherein Q has an average molecular weight of 200–800.

4. A compound according to claim 3 wherein R is a para-nitroanilino moiety, A is L-Arg and B is a peptide chain having two or three amino acid residues.

5. A compound according to claim 1 wherein B is a CHT, 4Hyp, 3Hyp, Ser, Thr or Tyr residue in which the OH side-group is protected in the form of an ether or ester.

6. A compound according to claim 1 wherein B is selected from the group consisting of
   (i) Aib, L-Ala, β-Ala, L-ATC, L-Aze, L-Abu, L-CHA, L-CHG, L-CHT, Cle, Gly, L-4Hyp, L-3-Hyp, L-Asp, L-Glu, L-Ile, L-Leu, L-Nle, L-Nva, L-Phe, L-Pip, L-Pro, MeGly, L-Ser, L-Thr, L-Tyr and L-Val residues,
   (ii) L-CHT, L-4Hyp, L-3Hyp, L-Ser, L-Thr and L-Tyr residues in which the OH side-group is protected in the form of an ester or ether group,
   (iii) L-Arg, L-Lys, L-His, L-Orn and L-Dbu residues in which each basic side-group is protected by Boc, Cbo, Adoc, Aoc, Fmoc, Foc, Iboc, Z, Z(p-Cl) or Z(p-OMe), and
   (iv) L-Asp or L-Glu residues in which the carboxylic acid side-group is esterified or amidified.

7. A compound according to claim 1 wherein B is a peptide residue and the amino acid containing the N-terminal end of said peptide residue which is bonded to the group Q via a carbonyl bridge is a non-basic α-amino acid residue selected from the group consisting of
   (i) Aib, Cle or Gly, and
   (ii) α-amino acid residue containing an asymmetric carbon atom and having the D or L configuration, the other amino acid residue or residues of the peptide chain B being Aib, Cle, Gly, or a non-basic α-amino acid having the L configuration.

8. A compound according to claim 1 wherein B is a dipeptide or tripeptide residue.

9. A compound according to claim 1 which is selected from the group consisting of
   (a) PEG$_{200}$(CO-Gly-L-Pro-L-Arg-pNA)$_2$,
   (b) PEG$_{600}$(CO-Gly-L-Pro-L-Arg-pNA)$_2$,
   (c) PEG$_{200}$(CO-D-Glu(OBzl)-L-Pro-L-Arg-pNA)$_2$,
   (d) PEG$_{200}$(CO-D-Nle-L-CHA-L-Arg-pNA)$_2$,
   (e) PEG$_{200}$(CO-D-Leu-Gly-L-Arg-pNA)$_2$, (f) PEG$_{200}$(CO-D-CHA-Gly-L-Arg-pNA)$_2$,
(g) PEG$_{300}$(CO-D-Leu-Gly-L-Arg-pNA)$_2$,
(h) PEG$_{400}$(CO-D-Leu-Gly-L-Arg-pNA)$_2$,
(i) PEG$_{200}$(CO-D-Nle-Gly-L-Arg-pNA)$_2$ and
(j) acid addition salts thereof.

10. A compound according to claim 1 wherein B is a monoamino acid residue selected from the group consisting of Ala, β-Ala, Cys, Gln, 4Hyp, 3Hyp, Leu, Met, Nle, Nva, Phe, Pro, MeGly, Ser, Tyr, Val, Asp, β-Asp, Glu, γ-Glu, ACC, AHX, Aib, ATC, Aze, Abu, 4Abu, CHA, CHG, CHT, Cle, Phg, Pip and Pyr.

11. A compound according to claim 1 where B is a monoamino acid residue selected from the group consisting of Arg, Lys, His, Orn and Dbu in which each basic side-group is blocked by Boc, Cbo, Adoc, Aoc, Fmoc, Foc, Iboc, Z, Z(p-Cl) or Z(p-OMe).

12. A compound according to claim 1 wherein B is Cys in which the SH side-group is protected.

13. A compound according to claim 1 in which B is an Asp or Glu residue in which the OH group of the carboxyl acid side-group is protected.

14. A compound according to claim 1 which is a symmetrical bipeptide selected from the group consisting of
(i) the compounds of the formula

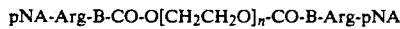
pNA-Arg-B-CO-O[CH$_2$CH$_2$O]$_n$-CO-B-Arg-pNA in which
B is a single bond, Aib, Cle, Gly, a non-basic monoamino acid residue having the L configuration, or a di- tripeptide residue in which the amino acid residue containing the N-terminal end of the peptide chain which is bonded to the carbonyl bridge, CO, is Aib, Cle, Gly or a non-basic α-amino acid having the L or D configuration, the other amino acid residue or residues of said peptide chain being one or more Aib, Cle, Gly or non-basic α-amino acid residues having the L configuration; and
n is an integer greater than or equal to 1, such that the average molecular weight of the group O[CH$_2$CH$_2$O]$_n$ is between about 60 and 600; and
(ii) their acid addition salts.

15. A compound according to claim 1 wherein R is a chromogenic, fluorogenic or radioactive amino-containing group which can be split off by enzymatic hydrolysis and which is capable of forming a colored, fluorescent or radioactive detectable compound.

16. A method for preparing a compound of formula I and its acid addition salts according to claim 1, said method comprising reacting an amino acid or peptide compound of the formula

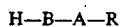
H—B—A—R (IV)

in which B, A and R are defined as indicated in claim 1 above, with a polyalkylene glycol dihalogenoformate of the formula

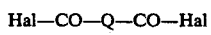
Hal—CO—Q—CO—Hal (V)

in which Hal is a halogen atom, especially F, Cl or Br and Q is defined as indicated in claim 1 above.

17. A method according to claim 16 wherein 2 mol of IV are reacted with 1 to 1.3 mol of V in an inert solvent at a temperature of 0° to 40° C., in the presence of a tertiary amine as a proton acceptor, in a molar ratio tertiary amine/compound IV of 1.7/1 to 3.6/1.

18. A method according to claim 16 wherein Hal is Cl.

19. A method of determining an enzyme involved in hemostasis, wherein a given amount of a compound of formula I or of one of its acid addition salts according to claim 1 is brought into contact, in an aqueous biological medium, with a test sample containing said enzyme.

20. A method according to claim 19 wherein a given amount of a compound of formula I or of one of its acid addition salts is brought into contact, in an aqueous biological medium, with a test sample containing said enzyme for at least 0.25 h at a temperature of between 15° and 40° C.

21. An assay kit for the determination of enzymes involved in hemostasis, which comprises at least one compound selected from the group consisting of the compounds of formula I and their acid addition salts according to claim 1 and a sample of an enzyme corresponding to the enzyme to be assayed.

* * * * *